United States Patent [19]
Lynn

[11] Patent Number: 5,114,400
[45] Date of Patent: May 19, 1992

[54] BLOOD WITHDRAWAL APPARATUS AND METHOD

[76] Inventor: Lawrence A. Lynn, 1275 Olentangy River Rd., Ste. 202, Columbus, Ohio 43212

[21] Appl. No.: 540,605

[22] Filed: Jun. 19, 1990

[51] Int. Cl.⁵ .............................................. A61M 31/00
[52] U.S. Cl. .................................... 604/53; 604/205; 604/283; 604/905
[58] Field of Search ............... 604/118, 119, 121, 201, 604/205, 246, 256, , 82, 83, 86, 87, 88, 244, 280, 283, 167, 905, 52, 53, 35

[56] References Cited

U.S. PATENT DOCUMENTS

| | | | |
|---|---|---|---|
| 4,022,205 | 5/1977 | Tenczar | 604/905 |
| 4,799,494 | 1/1989 | Wang | 604/51 |
| 4,865,583 | 9/1989 | Tu | 604/53 |
| 4,935,010 | 6/1990 | Cox et al. | 604/905 |
| 4,981,140 | 1/1991 | Wyatt | 604/201 |
| 4,981,469 | 1/1991 | Whitehouse et al. | 604/283 |
| 4,986,278 | 1/1991 | Ravid et al | 604/121 |
| 4,998,927 | 3/1991 | Vaillancourt | 604/283 |

FOREIGN PATENT DOCUMENTS

| | | |
|---|---|---|
| 0367549 | 5/1990 | European Pat. Off. |
| WO91/00115 | 6/1990 | PCT Int'l Appl. |

*Primary Examiner*—Gene Mancene
*Assistant Examiner*—Michael Lynch
*Attorney, Agent, or Firm*—Nixon & Vanderhye

[57] ABSTRACT

A blood withdrawal apparatus and method in which a blunt cannula or needle penetrates an elastomeric septum into a pressurized flow channel such as an arterial line. After blood is withdrawn into the attached syringe, the needle tip is withdrawn into the septum until an indication is detected, for example by engagement of a detent on a shroud surrounding the cannula or needle with a detent on the housing for the septum. The nurse can then depressurize the syringe by operating the piston and thus prevent blood spurt when the needle tip is subsequently fully withdrawn from the septum.

34 Claims, 2 Drawing Sheets

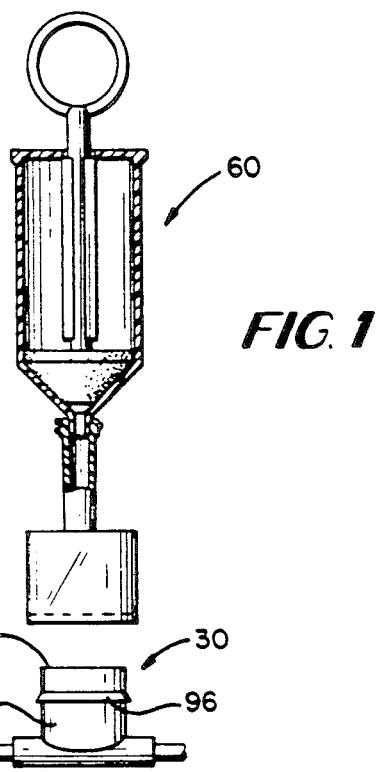
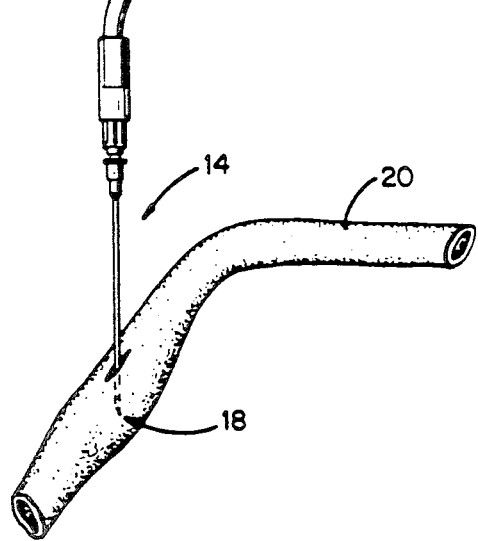
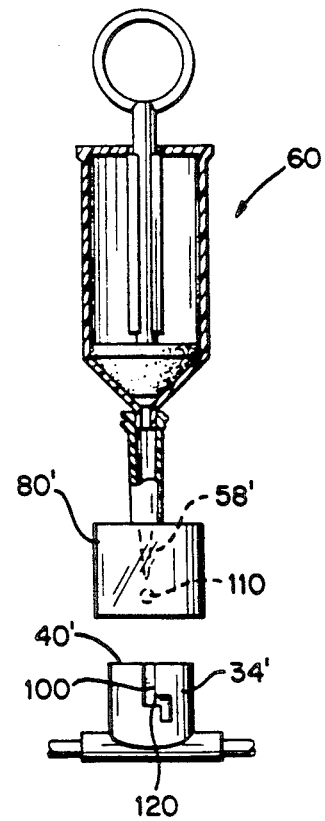
FIG. 1
FIG. 4 ial line. This design substantially reduces the risk of needle-
BLOOD WITHDRAWAL APPARATUS AND METHOD

BACKGROUND AND SUMMARY OF THE INVENTION

The invention relates to aspiration of blood samples through an elastomeric septum from pressurized flow channels such as arterial lines.

Such aspiration has become an important method of blood sampling. In this sampling technique, a needle or cannula is inserted into the flow channel through the elastomeric septum, and blood is withdrawn into a blood collection device such as a syringe attached to the needle or cannula. The needle tip is thus inserted into the flow channel through the elastomeric septum, and blood is drawn into the syringe through the bore of the needle. The needle is then removed from flow channel and septum and the sample is transported to the lab for analysis.

One major problem which exists with this technique is that the elevated pressure within the flow channel is transmitted through the bore of the needle into the syringe. Since syringes and needles commonly have a small amount of dead air space within them, a bubble of air will be displaced into and trapped within the syringe when blood is drawn into the syringe through the needle. The transmitted pressure from the flow channel into the syringe through the needle bore can compress the air bubble when the needle bore is in fluid communication with the flow channel. When the needle is removed from the pressurized flow channel and the needle tip exits the septum, the bore of the needle is exposed to atmospheric pressure which may be substantially lower than the pressure within the syringe which has now been pressurized. The pressurized air bubble within the syringe expands rapidly upon the reduction of pressure at the opening of the bore of the needle near the needle tip thereby forcing blood out of the needle through the exposed opening. This rapid expansion of the bubble within the syringe therefore causes blood to spurt from the needle tip. This spurt of potentially infectious blood may strike the nurse or spray onto the bedsheets resulting in substantial blood exposure to hospital personnel.

Pending U.S. patent application Ser. No. 07/302,835 filed Jan. 27, 1989, describes a novel aspiration system comprising an aspirator receiver and blunt aspirator for use with a pressurized flow channel such as an arterial line. This design substantially reduces the risk of needlestick injury but is still subject to the blood spurting problem as described above. The present invention is an improved blood aspiration system and technique which is designed to eliminate the blood spurting problem.

Blood cannot spurt if the pressure in the syringe is relieved while the needle tip is occluded by the septum. Therefore, detecting and indicating when the tip is so occluded is very useful.

The blood aspiration system of this invention provides an occlusion indicator as well as an aspirator receiver means in fluid communication with a flow channel. The flow channel is connectable to a catheter in fluid communication with a blood vessel having an elevated internal fluid pressure. The system further includes a blood aspirator having a proximal and a distal end and a bore extending from the proximal end to an distal opening near the distal end. The occlusion indicator indicates when the aspirator is positioned within the septum such that distal opening of the bore of the aspirator is occluded.

In the preferred embodiment the aspirator receiver includes a housing having a passage extending from a proximal opening to an interface with the flow channel. The passage is occluded with an elastomeric septum having a perforation for receiving a blood aspirator which is preferably a needle having a blunt distal tip. The blunt needle has a bore extending from a proximal hub to an opening near the distal tip of the needle. The hub is preferably connectable to and may be permanently attached to a conventional syringe having a piston and internal chamber. The needle further includes means defining a space extending distally about the needle. The space defining means is preferably a cylindrical shroud sized to be received over the housing of the aspirator receiver. The shroud is connected to the needle and preferably extends beyond the needle tip.

A needle occlusion indication means indicates the position of the needle within the septum wherein the tip of the needle is occluded, and is preferably provided on the housing, but may be provided along the outer surface of the needle. In the preferred embodiment, the occlusion indicator means comprises a detent on the outer surface of the housing of the aspirator receiver and a corresponding detent on the inner surface of the shroud. The detents are specifically positioned such that withdrawal of a needle which has been received over the aspirator receiver is inhibited at a position wherein the distal opening of the needle bore is fully within the elastomeric septum and is occluded by the septum. This, therefore, provides a tactile indication that the needle tip is located at a position wherein the opening near the tip is occluded. At this point the nurse can stop withdrawing the needle and hold the shroud and needle in position while retracting the syringe piston. This will effectively decompress any trapped air within the chamber of the syringe. The nurse can then apply additional force to withdraw the shrouded needle completely from the septum.

DESCRIPTION OF THE PREFERRED EMBODIMENT

Figure 2:
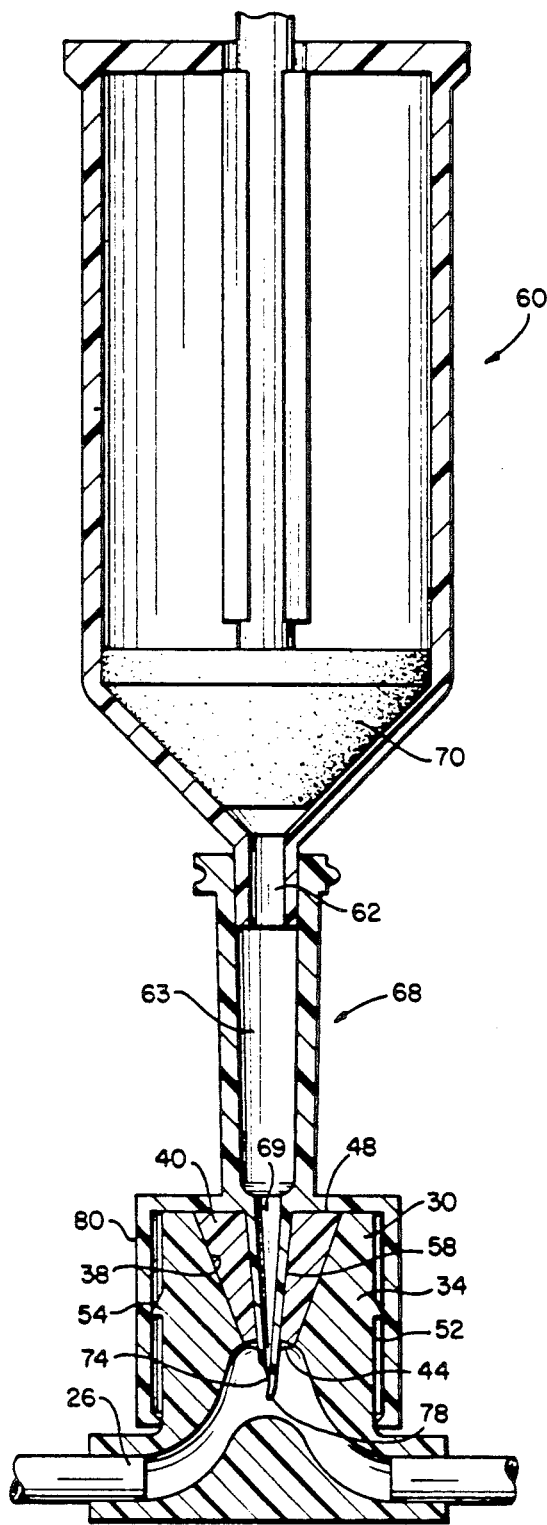

Referring now to FIGS. 1-4 the blood aspiration system with aspirator occlusion indicator 10 is shown generally. Catheter 14 is shown with its tip 18 within a blood vessel 20 of a patient. Conduit 24 is connected to catheter 14 placing flow channel 26 (FIG. 2) of conduit 24 into fluid connection with blood vessel 20 (FIG. 1). The conduit 24 extends to an aspirator receiver 30 integral with conduit 24. Housing 34 of aspirator receiver 30 has passage 38 occluded by elongated elastomeric septum 40 extending from a flow channel interface 44 to an atmospheric interface 48. A central perforation 50 (FIG. 3) through septum 4 extends from the atmospheric interface 48 of the septum 4 to the flow channel interface 44. The outer surface 52 of housing 34 has annular housing detent 54.

The blunt needle aspirator 58 is shown connected to a conventional syringe 60. The syringe 60 includes syringe tip 62 shown inserted into dead space 63 and needle hub 68. A needle bore 69 extends from hub 68 to a distal bore opening 74 near needle tip 78. Piston 70 is mounted within syringe 60 defining syringe chamber 79 below piston 70. Needle 58 is integral with shroud 80 which extends beyond needle tip 78 to define a space 84. The inner surface 86 of shroud 80 has annular shroud detent 90. Shroud 80 is sized to be snugly received over housing 34. The housing detent 54 is positioned along the outer surface 52 of housing 34 such that the distal opening 74 of needle bore 69 is occluded by septum 40 when the detents 54 and 90 are engaged as in FIG. 3.

Figure 3:
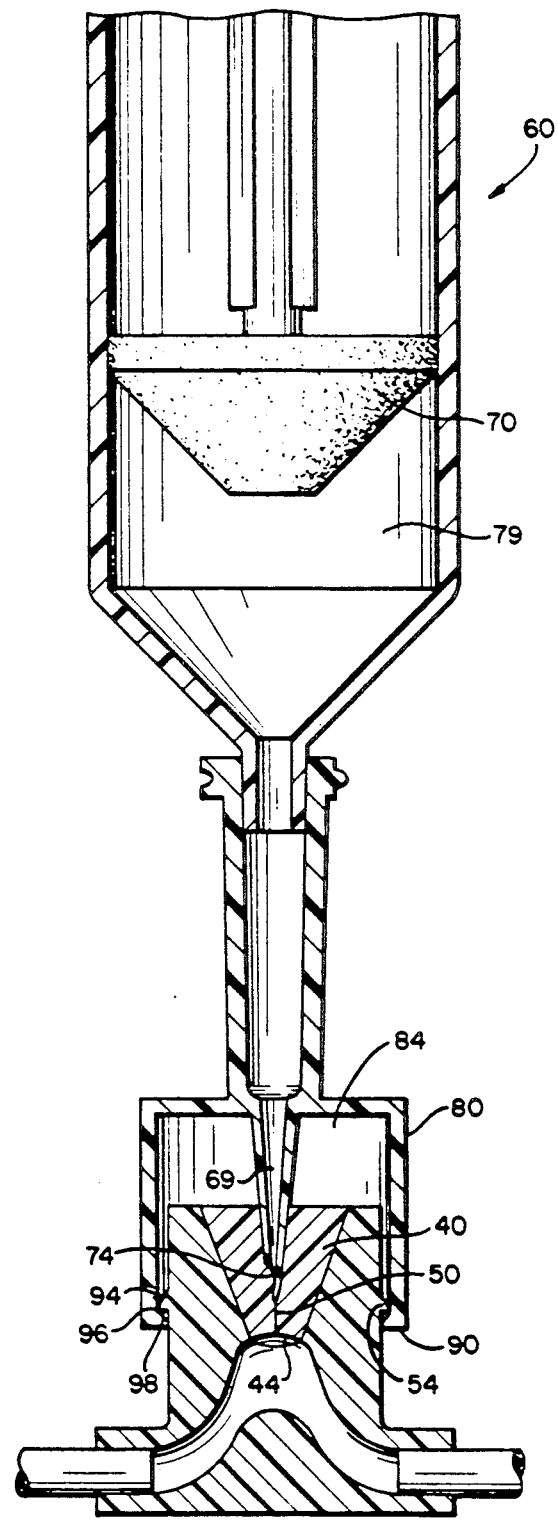

In the preferred embodiment, the housing detent 54 is shaped to provide an initial slow elevation 94, a summit 96, and a sharp descent 98. Shroud detent 90 is therefore easily pushed past housing detent 54 as the needle tip 78 is advanced through the perforation 50 of septum 40, as the needle 58 is advanced to the position of FIG. 2, wherein the opening 74 of the needle bore 69 is within the flow channel 26 when needle tip 78 is maximally advanced through septum 40. The distance from shroud detent 90 to housing detent 54 is greater than the distance from the septum flow channel interface 44 to the distal bore opening 74. However, during the withdrawal of the needle 58 from the septum 40, the withdrawal is inhibited when the shroud detent 90 engages the housing detent 54, as shown in FIG. 3. This provides a tactile indication that the distal bore opening 74 of the needle bore 69 is in a position such that the bore opening 74 is occluded by the septum 40, as shown in FIG. 3. At this point the syringe chamber 79 is completely sealed so that withdrawal of the piston 70 will not draw blood or air into the syringe 60 but will rather induce a negative pressure within the syringe chamber 79.

This negative pressure will be transmitted to the air bubble (not shown) which is commonly trapped within the syringe chamber 79. As will be described, this trapped bubble now will contain a partial vacuum rather than an elevated pressure. The bubble will therefore enlarge when the bore opening 74 exits the septum atmospheric interface 48 upon further withdrawal of the needle 58. This causes the syringe chamber 79 to actually suck residual blood from the atmospheric interface 48 of the septum 40 as the bubble contracts in response to the relief of the relative vacuum within the bubble by air entry through the bore opening 74. The relative ease with which the piston 70 moves within the syringe 60 will determine, in part, the extent to which the bubble will retain a negative pressure since this negative pressure will have a tendency to cause the piston 70 to advance toward the negative pressure to relieve it. In any case, the positive pressure which causes the spurt of blood will be eliminated by this novel design and technique and at least some negative pressure is likely to remain within the bubble.

The unique system is operated by inserting the blunt needle 58 attached to the syringe 60 through the perforation 50 in the septum 40 so that the distal opening 74 of the needle bore 69 is in fluid connection with the pressurized blood within the flow channel 26. The piston 70 of the syringe 60 is then retracted to cause blood to enter the chamber 79 of the syringe 60. (In practice the elevated pressure within the flow channel 26 may cause the piston 70 to be forced upward without manual retraction.) Some air will enter the syringe chamber 79 from the dead space 63 within hub 68 and from within needle bore 69. When the nurse stops retracting piston 70 of the syringe 60, the pressure within the flow chamber 26 will rapidly equilibrate with the syringe chamber 79 effectively compressing the air bubble trapped within the syringe chamber 79. The nurse then begins to withdraw the syringe 60 and the attached needle 58 out of the septum 40 until the nurse feels shroud detent 90 engaging the housing detent 54. The nurse then stops withdrawing the syringe 60. Then while holding the syringe 60 and needle 58 in place the nurse manually retracts piston 70. The distal opening 74 of the needle bore 69 is occluded by the septum 40 when the detents are so engaged, therefore, neither air nor blood can enter the syringe chamber 79. The retraction of the piston 70 will, therefore, depressurize the syringe chamber 79 and actually induce a negative pressure within the trapped air bubble. The nurse then further withdrawals the syringe 60 and the attached shrouded needle 58 past the housing detent 54 until the needle tip 78 exits the septum 40. With this technique, the needle bore opening 74 will exit the septum 40 without the spurt of blood which so often accompanies conventional technique.

Many modifications can be made to provide visual, tactile, auditory, or other indication that the needle bore opening 74 is occluded. A visual indicator, such as a red line (not shown) could be provided on the needle 58 or the housing 34 at a predetermined point to indicate occlusion of the distal opening 74 of the needle bore 69. Also a variety of detents can be provided for tactile and/or auditory indication of needle bore occlusion. For example, as in FIG. 4, the housing 34' may have a shallow slot 100 to receive a post 110 on the inner surface of shroud 80'. The slot 100 can angulate sharply at a predetermined angle point 120 along the housing 34'. At the position at which the post 110 engages the angle point 120 during withdrawal of the needle 58' from the septum 40', the distal opening (not shown) in the needle bore (not shown) is occluded by the septum 40' in a manner similar to the that described for the preferred embodiment. The nurse is therefore notified that, at this position, withdrawal of the needle 58' should temporarily stop and the syringe chamber should be decompressed, as previously discussed, before the shroud 80' is rotated past the angle point 120 and is completely removed from over housing 34'.

What is claimed is:

1. For use in aspirating a sample of blood from a flow channel into an interior chamber of a blood storage container, the flow channel being adapted for communication through a catheter with the lumen of a blood vessel of a patient, the blood vessel lumen containing blood under pressure, an aspiration assembly comprising:

a housing having an internal passage for communication with the flow channel;

a cannula having a distal tip, first and second openings, and a bore through said cannula extending between said first and second openings, said second opening being located adjacent said distal tip of said cannula;

an elastomeric element in said housing normally occluding said internal passage and adapted to be penetrated by said cannula so that at least a portion of said cannula can enter and pass through said element to locate said second opening in communication with the flow channel so that blood from the flow channel can enter said bore through said second opening for passage through said bore and through said first opening;

means carried by the cannula for connecting said cannula to the blood storage container so that said cannula bore lies in communication with the interior chamber of the blood storage container through said first opening;

means carried by said housing responsive to at least partial withdrawal of said cannula from said housing for precluding communication between said cannula bore and both the flow channel and ambient atmosphere; and means carried by at least one of said cannula and said housing for indicating when communication between said cannula and the flow channel is precluded.

2. An assembly according to claim 1 in combination with said blood storage container having said interior chamber and including means coupled to said blood storage container for inducing a negative pressure within said interior chamber of said blood storage container.

3. An assembly according to claim 2 wherein said blood storage container comprises a syringe and said negative pressure inducing means comprises a piston for said syringe in said interior chamber.

4. An assembly according to claim 1 wherein said elastomeric element seals about said second opening of said cannula when said second opening is positioned within said element during said at least partial withdrawal of said cannula from said element to preclude communication between said cannula bore and the flow channel.

5. An assembly according to claim 4 wherein said indicating means further indicates when said second opening of said cannula is sealed by said elastomeric element.

6. An assembly according to claim 1 further including a shroud connected to said cannula and extending in a direction toward said distal tip and about said cannula, said shroud being sized to receive at least a portion of said housing when said elastomeric element is penetrated by said cannula.

7. An assembly according to claim 6 wherein said indicating means comprises detents on said shroud and said housing, respectively, said detents being engageable with one another during said at least partial withdrawal of said cannula from said element, when communication between said cannula bore and the flow channel is precluded.

8. An assembly according to claim 7 wherein said elastomeric element seals about said second opening of said cannula when said second opening is positioned within said element during said at least partial withdrawal of said cannula from said element, said detent on said shroud and said detent on said housing engaging one another during said at least partial withdrawal of said cannula from said element when said elastomeric element seals about said second opening.

9. An assembly according to claim 1 wherein said elastomeric element seals against said cannula about said second opening when said second opening is positioned within said element, and means cooperable between said cannula and said housing for inhibiting withdrawal of said cannula relative to said elastomeric element when said second opening is sealed by said element.

10. An assembly according to claim 1 wherein said elastomeric element has an outer face, an inner interface in the flow channel and a normally sealed perforation extending from said outer face through said element to said interface for receiving said cannula.

11. In an apparatus for aspiration of a sample of blood from a flow channel into an interior chamber of a blood storage container, the flow channel being adapted for communication through a catheter with the lumen of a blood vessel of a patient, the blood vessel lumen containing blood under pressure, an aspiration assembly comprising:

a housing having an internal passage in communication with said flow channel;

a cannula having a distal tip, first and second openings, and a bore through said cannula extending between said first and second openings, said second opening being located adjacent said distal tip of said cannula;

an elastomeric element in said housing normally occluding said internal passage and adapted to be penetrated by said cannula so that at least a portion of said cannula can enter and pass through said element to locate said second opening in communication with said flow channel so that blood from said flow channel can enter said bore through said second opening for passage through said bore and through said first opening;

means carried by the cannula for connecting said cannula to said blood storage container so that said cannula bore lies in communication with said interior chamber of said blood storage container through said first opening;

means responsive to at least partial withdrawal of said cannula from said flow channel portion and from said element for precluding communication between said cannula bore and said flow channel; and means cooperable between said cannula and said housing for positively inhibiting withdrawal of said cannula from said element when communication between said cannula and said flow channel portion is precluded.

12. Apparatus according to claim 11 wherein said elastomeric element seals about said second opening of said cannula when said second opening is positioned within said element during said at least partial withdrawal of said cannula from said element to preclude communication between said cannula bore and said flow channel, said cooperable means including detents on said cannula and said housing spaced one from the other when said second opening is located in communication with said flow channel a distance such that withdrawal of said cannula through a distance corresponding to the distance between said second opening when in communication with said flow channel portion and when sealed causes said detents to engage one another and inhibit withdrawal of said cannula from said element.

13. A method of aspirating a blood sample from a flow channel through an aspirator assembly into an interior chamber of a blood storage container, the aspirator assembly including a housing in communication with the flow channel, an elastomeric element carried by said housing and a cannula having a bore, comprising the steps of:

inserting the cannula into the elastomeric element to establish communication between the bore of the cannula and the flow channel;

aspirating a volume of blood from the flow channel into said blood storage container through said cannula;

partially withdrawing said cannula from said element until said second opening is sealed from said flow channel by said element;

reducing the pressure within said interior of said blood storage container after said second opening is sealed by said element; and completing the withdrawal of said cannula from said element.

14. A method according to claim 13 wherein said blood storage container comprises a syringe having a barrel and a piston and a handle for manual operation of the piston and the step of reducing the pressure includes retracting the piston relative to the barrel.

15. A method according to claim 13 including the step of indicating when said second opening is sealed by said element.

16. A method according to claim 13 including discontinuing the withdrawal of said cannula from said element after said second opening is sealed by said element and wherein the step of reducing the pressure is accomplished before the step of completing the withdrawal is undertaken.

17. A method of blood aspiration through a cannula into a syringe from a pressurized blood flow channel having an elastomeric septum in contact with the blood in said flow channel, comprising the steps of:

inserting said cannula through said septum to establish communication with said flow channel;

aspirating a volume of blood from said flow channel into said syringe through said cannula;

displacing said cannula and said septum relative to one another such that said cannula is sealed from said flow channel by said septum;

inducing negative pressure within said syringe when said cannula is sealed from said flow channel; and separating said cannula and said septum one from the other to expose said cannula to atmosphere without forcing blood out of the cannula.

18. The method of claim 17 including the step of tactilely indicating when said cannula is sealed from said flow channel.

19. The method according to claim 18 including the step of inhibiting relative displacement between said cannula and said septum when said cannula is sealed from said flow channel.

20. A method of blood aspiration through an aspirator into a syringe from a pressurized flow channel connected to an aspirator receiver, the aspirator receiver having an elastomeric septum and a detent, the aspirator having a second detent, and including the steps of:

inserting said aspirator through said septum to establish communication with said flow channel;

aspirating a volume of blood from said flow channel into said syringe through said aspirator;

partially withdrawing said aspirator from the septum until said detents engage one another;

sealing the aspirator by said septum in response to partial withdrawal of said aspirator from said septum, said detents being located relative to one another for engagement when the septum seals said aspirator;

inducing negative pressure within said syringe while said aspirator is sealed by said septum; and completing the withdrawal of said aspirator from said septum.

21. A method of blood aspiration through a cannula into a syringe from a pressurized blood flow channel in communication with the lumen of a blood vessel of the patient and through a septum, comprising the steps of:

inserting said cannula through said septum to establish communication with the pressurized blood in the flow channel;

aspirating a volume of pressurized blood from the flow channel into said syringe through said cannula;

isolating the pressurized blood in the syringe from the pressurized blood in the blood vessel of the patient;

reducing the pressure within the syringe after isolating the pressurized blood in the syringe from the pressurized blood in the patient's blood vessel; and subsequently, separating the cannula and the septum one from the other to expose the cannula to atmosphere without forcing blood out of the cannula upon separation.

22. In a blood aspirator assembly having a storage container for aspirated blood, the said container having means to reduce pressure upon a volume of blood within the container, and a catheter for connection to the blood vessel of a patient, improvements in blood withdrawal indication assembly comprising:

(a) a blood withdrawing cannula having a distal end, the cannula having a bore sized to permit blood flow therethrough, the cannula bore having a first opening and means for placing the first opening in liquid flow connection with the blood storage container, the cannula bore having a second opening located distally of the first opening;

(b) a housing having a blood flow channel therethrough, the housing having means for receiving blood flow from the catheter into the flow channel;

(c) the housing having associated therewith a portion having means for receiving the cannula therethrough to permit the second cannula opening to be placed in a first position relative to said housing portion so as to be in blood flow communication with the said flow channel;

(d) the said housing portion having associated therewith means for occluding blood flow through the cannula bore as well as precluding communication between said cannula bore and ambient atmosphere when the cannula is placed in a second position relative to said housing portion; and (e) means for giving sensory indication to the operator of when the cannula is in said second position so that, while blood flow through the cannula is occluded, the pressure of the blood in the storage container can be reduced.

23. The blood withdrawal indication assembly of claim 22 wherein the means for giving sensory indication comprises means associated with the cannula for movement with the cannula.

24. The blood withdrawal indication assembly of claim 23 wherein the means for giving sensory indication comprises means associated with the housing for interacting with the means associated with cannula movement.

25. The blood withdrawal indication assembly of claim 24 wherein the means associated with cannula movement comprises a first detent associated with the cannula to move therewith, and the means for interacting comprises a second detent associated with the housing, the first detent having means for being positioned in association with the cannula and the second detent having means for being positioned in association with the housing so that the detents are not in contact with one another when the cannula bore is in liquid flow connection with the said flow channel, and so that the first and second detents engage each other when the cannula and housing portion are in the said second position that occludes blood flow through the cannula bore, so that such engagement of the detents impedes movement of the cannula away from the housing portion to provide said sensory indication.

26. The blood withdrawal indication assembly of claim 22 wherein the means for occluding blood flow comprises the housing portion comprising resilient material.

27. A method of aspirating blood with an aspirating means and of withdrawal of the aspirating means, for use in aspiration from a blood flow channel, which channel is in liquid flow communication with a blood vessel of the body, the aspirating means being in liquid flow communication with a blood storage container, the container having means to reduce pressure upon a volume of blood within the container, the aspirating means having a bore sized to allow blood flow therethrough, the bore having a first opening for liquid flow communication with the storage container and a second opening located distally of the first opening, the blood flow channel having associated therewith means for receiving the aspirating means to permit the second cannula opening to be placed in a first position relative to said flow channel so as to be in liquid flow communication with said flow channel, and said blood flow channel having means for occluding blood flow through the aspirating bore when the aspirating means is placed in a second position relative to said flow channel, the method comprising the steps of:
  (a) inserting the aspirating means through the said receiving means;
  (b) placing the second aspirating bore in liquid flow connection with the blood vessel through said blood flow channel;
  (c) aspirating blood from the blood flow channel through the aspirating means and into the blood storage container;
  (d) occluding the second opening from fluid connection with the blood vessel;
  (e) while said aspirating means is in said second position, operating the means for reducing pressure so that the pressure within the blood storage container is reduced;
  (f) after the pressure reducing step has been performed, then withdrawing the aspirating means away from said blood flow channel and from said receiving means to position the second opening so that it is no longer occluded.

28. The blood aspirating and aspirating means withdrawal method of claim 27 wherein in the preamble said means for occluding blood flow comprises a housing, said housing comprising resilient material; wherein the step of occluding blood flow through said aspirating means bore comprises the step of said resilient material sealing about the second opening of the bore to occlude blood flow through the bore.

29. The blood aspirating and aspirating means withdrawal method of claim 28 wherein in the preamble the method is for use with a means for sensory indication of when the aspirating means is in said second position to occlude blood flow; further comprising the step of signaling with the sensory indication means when the aspirating means is in said second position.

30. The blood aspirating and aspirating means withdrawal method of claim 29 wherein in the preamble the method is for use with means for blocking movement of the aspirating means in a direction away from the blood flow channel; further comprising the step of blocking movement of the aspirating means away from the blood flow channel when the aspirating means bore is occluded by said occluding means.

31. The blood aspirating and aspirating means withdrawal method of claim 30 wherein the step of blocking movement of the aspirating means and the step of signaling are the same step.

32. The blood aspirating and aspirating means withdrawal method of claim 30 further comprising the step of releasing the blocking of movement of the aspirating means by rotating the aspirating means relative to means for occluding blood flow.

33. The blood aspirating and aspirating means withdrawal method of claim 27 wherein in the preamble the means for reducing pressure in the blood storage container comprises a piston; wherein the step of reducing the pressure within the container is performed by retracting the piston relative to the blood storage container.

34. A method of aspirating blood with an aspirating means and of withdrawal of the aspirating means, for use in aspiration from a blood flow channel, which channel is in liquid flow communication with a blood vessel of the body, the aspirating means being in liquid flow communication with a blood storage container, the container having means to reduce pressure upon a volume of blood within the container, the aspirating means having a bore sized to allow blood flow therethrough, the bore having a first opening for liquid flow communication with the storage container and a second opening located distally of the first opening, the blood flow channel having associated therewith means for receiving the aspirating means to permit the second cannula opening to be placed in a first position relative to said flow channel so as to be in liquid flow communication with said flow channel, the method comprising the steps of:
  (a) inserting the aspirating means through the said receiving means;
  (b) placing the second aspirating bore in liquid flow connection with the blood vessel through said blood flow channel;
  (c) aspirating blood from the blood flow channel through the aspirating means and into the blood storage container;
  (d) occluding the second opening from fluid connection with the blood vessel;
  (e) while said second opening is occluded from said blood vessel, operating the means for reducing pressure so that the pressure within the blood storage container is reduced;
  (f) after the pressure reducing step has been performed, then withdrawing the aspirating means away from said blood flow channel and from said receiving means.

* * * * *